United States Patent [19]

Unger

[11] Patent Number: 5,281,408
[45] Date of Patent: Jan. 25, 1994

[54] LOW DENSITY MICROSPHERES AND THEIR USE AS CONTRAST AGENTS FOR COMPUTED TOMOGRAPHY

[76] Inventor: Evan C. Unger, 13365 E. Camino La Cebadilla, Tucson, Ariz. 85749

[21] Appl. No.: 980,594

[22] Filed: Jan. 19, 1993

Related U.S. Application Data

[62] Division of Ser. No. 680,984, Apr. 5, 1991, Pat. No. 5,205,290.

[51] Int. Cl.$^5$ .................. G01N 23/04; A61K 9/14; A61K 9/16; A61K 9/50
[52] U.S. Cl. .................. 424/4; 128/654; 424/489; 424/497; 424/501; 428/402
[58] Field of Search .......... 424/4, 489, 497, 501; 128/654; 428/402

[56] References Cited

U.S. PATENT DOCUMENTS

| | | | |
|---|---|---|---|
| 3,015,128 | 1/1962 | Sommerville et al. | 18/2.6 |
| 3,293,114 | 12/1966 | Kenaga et al. | 162/168 |
| 3,479,811 | 11/1969 | Walters | 57/153 |
| 3,488,714 | 1/1970 | Walters et al. | 161/161 |
| 3,594,326 | 7/1971 | Himmel et al. | 252/316 |
| 3,615,972 | 10/1971 | Morehouse et al. | 156/79 |
| 3,732,172 | 5/1973 | Herbig et al. | 252/316 |
| 3,945,956 | 3/1976 | Garner | 260/2.5 B |
| 3,960,583 | 6/1976 | Netting et al. | 106/122 |
| 4,108,806 | 8/1978 | Cohrs et al. | 521/54 |
| 4,138,383 | 2/1979 | Rembaum et al. | 260/29.7 H |
| 4,179,546 | 12/1979 | Garner et al. | 521/56 |
| 4,420,442 | 12/1983 | Sands | 264/13 |
| 4,421,562 | 12/1983 | Sands et al. | 106/75 |
| 4,540,629 | 9/1985 | Sands et al. | 428/402 |
| 4,549,892 | 10/1985 | Baker et al. | 65/21.4 |
| 4,681,119 | 7/1987 | Rasor et al. | 128/660 |
| 4,789,501 | 12/1988 | Day et al. | 252/645 |
| 4,822,534 | 4/1989 | Lencki et al. | 264/4.3 |
| 4,898,734 | 2/1990 | Mathiowitz et al. | 424/426 |
| 4,900,540 | 2/1990 | Ryan et al. | 424/9 |
| 5,019,370 | 5/1991 | Jay et al. | 424/4 |
| 5,078,994 | 1/1992 | Nair et al. | 424/501 |
| 5,088,499 | 2/1992 | Unger | 128/662.02 |
| 5,186,922 | 2/1993 | Shell et al. | 128/654 |
| 5,205,290 | 4/1993 | Unger | 128/653.4 |

FOREIGN PATENT DOCUMENTS 62-286534 12/1987 Japan.
1044680 10/1966 United Kingdom.

OTHER PUBLICATIONS

Chang et al., Canadian J. of Physiology and Pharmacology, vol. 44, pp. 115-128 and p. 513 (1966).
Chang, Science, vol. 146, pp. 524-525 (1964).
Deasy, Microencapsulation and Related Drug Processes, vol. 20, Chs. 9 and 10, pp. 195-240 (Marcel Dekker, Inc., N.Y.) (1983).
Yeung et al., J. Microencapsulation, vol. 5, pp. 331-337 (1988).

Primary Examiner—Gary Hollinden
Attorney, Agent, or Firm—Woodcock Washburn Kurtz Mackiewicz & Norris

[57] ABSTRACT

Substantially homogeneous aqueous suspensions of low density microspheres are presented as contrast media for imaging the gastrointestinal tract and other body cavities using computed tomography. In one embodiment, the low density microspheres are gas-filled. With computed tomography, the contrast media serve to change the relative density of certain areas within the gastrointestinal tract and other body cavities, and improve the overall diagnostic efficacy of this imaging method.

16 Claims, No Drawings

LOW DENSITY MICROSPHERES AND THEIR USE AS CONTRAST AGENTS FOR COMPUTED TOMOGRAPHY

RELATED APPLICATION

This application is a divisional of U.S. Ser. No. 07/680,984, filed Apr. 5, 1991; now U.S. Pat. No. 5,205,290.

BACKGROUND OF THE INVENTION

Computed tomography (CT) is a widespread diagnostic imaging method which measures, in its imaging process, the radiodensity (electron density) of matter. This radiodensity is depicted using CT in terms of Hounsefield Units (HU). Hounsefield Units, named after the inventor of the first CT scanner, reflect the relative absorption of CT X-rays by matter, the absorption being directly proportional to the electron density of that matter. Water, for example, has a value of 0 HU, air a value of $-1000$ HU, and dense cortical bone a value of $+1000$ HU. Because of the similarity in density of various tissues in the body, however, contrast agents have been sought to change the relative density of different tissues, and improve the overall diagnostic efficacy of this imaging method.

In the search for contrast agents for CT, researchers have generally sought to develop agents that will increase electron density in certain areas of a region of the body (positive contrast agents). Barium and iodine compounds, for example, have been developed for this purpose. For the gastrointestinal tract, barium sulfate is used extensively to increase the radiodensity of the bowel lumen on CT scans. Iodinated water soluble contrast media are also used to increase density within the gastrointestinal tract, but are not used as commonly as the barium compounds, primarily because the iodine preparations are more expensive than barium and prove less effective in increasing radiodensity within this region of the body.

Despite their widespread use, however, barium and iodine compounds are suboptimally effective as gastrointestinal contrast agents for CT. For example, if the concentration is too low, there is little contrast. Conversely, if the concentration is too high, then these radiodense contrast agents cause beam hardening artifacts which are seen as streaks on the CT images. It is also difficult to visualize the bowel mucosa with either the barium or iodine contrast agents.

In an attempt to improve upon the efficacy of contrast agents for the gastrointestinal tract, lipid emulsions that are capable of decreasing electron density (negative contrast agents) have been developed. Because lipids have a lower electron density than water, lipids provide a negative density on CT (a negative HU value). While these lipid emulsions appear to be more effective than the barium and iodine agents at improving visualization of the mucosa of the bowel, these contrast agents have limitations. First, there is a limitation to the concentration of lipid which a patient can tolerably drink, which puts a limit on the change in density (or HU) which the lipid based CT contrast agent can provide. Lipid emulsions are also frequently expensive. Furthermore, these lipid formulations are generally perishable, which provides for packaging and storage problems.

New and/or better contrast agents for computed tomography imaging are needed. The present invention is directed toward this important end.

SUMMARY OF THE INVENTION

The present invention is directed to computed tomography imaging, and more particularly to the use of a contrast medium comprising a substantially homogeneous aqueous suspension of low density microspheres to image the gastrointestinal region and other body cavities of a patient. In one embodiment, the low density microspheres are gas-filled.

Specifically, the present invention pertains to methods of providing an image of the gastrointestinal region or other body cavities of a patient comprising (i) administering to the patient the aforementioned contrast medium, and (ii) scanning the patient using computed tomography imaging to obtain visible images of the gastrointestinal region or other body cavities.

The present invention is further directed to methods for diagnosing the presence of diseased tissue in the gastrointestinal region or other body cavities of a patient comprising (i) administering to the patient the aforementioned contrast medium, and (ii) scanning the patient using computed tomography imaging to obtain visible images of any diseased tissue in the patient.

The present invention also provides diagnostic kits for computed tomography imaging of the gastrointestinal region or other body cavities which include the subject contrast medium.

DETAILED DESCRIPTION OF THE INVENTION

A wide variety of different low density microspheres may be utilized in the present invention. Preferably, the microspheres (which are small spheres having a central void or cavity), are composed of biocompatible synthetic polymers or copolymers prepared from monomers such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, $\epsilon$-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-aminobenzylstyrene, sodium styrene sulfonate, sodium 2-sulfoxyethylmethacrylate, vinyl pyridine, aminoethyl methacrylates, 2-methacryloyloxy-trimethylammonium chloride, and polyvinylidene, as well polyfunctional crosslinking monomers such as N,N'-methylenebisacrylamide, ethylene glycol dimethacrylates, 2,2'-(p-phenylenedioxy)-diethyl dimethacrylate, divinylbenzene, triallylamine and methylenebis-(4-phenyl-isocyanate), including combinations thereof. Preferable polymers include polyacrylic acid, polyethyleneimine, polymethacrylic acid, polymethylmethacrylate, polysiloxane, polydimethylsiloxane, polylactic acid, poly($\epsilon$-caprolactone), epoxy resin, poly(ethylene oxide), poly(ethylene glycol), and polyamide (nylon). Preferable copolymers include the following: polyvinylidene-polyacrylonitrile, polyvinylidene-polyacrylonitrile-polymethylmethacrylate, and polystyrene-polyacrylonitrile. A most preferred copolymer is polyvinylidene-polyacrylonitrile. The term biocompatible, as used herein in conjunction with the terms monomer or polymer, is employed in its conventional sense, that is, to denote polymers that do not substantially interact with the tissues, fluids and other components of the body in a adverse fashion in the particular application of interest, such as the aforementioned monomers and polymers. Other suitable biocompatible monomers and polymers will be readily apparent to those skilled in the art, once armed with the present disclosure.

The microspheres of the present invention are low density. By low density, it is meant that the microspheres of the invention have an internal void (cavity) volume which is at least about 75% of the total volume of the microsphere. Preferably, the microspheres have a void volume of at least about 80%, more preferably at least about 85%, even more preferably at least about 90%, of the total volume of the microspheres.

The microspheres may be of varying size, provided they are low density. Suitable size microspheres include those ranging from between about 1 and about 1000 microns in outside diameter, preferably between about 5 and about 70 microns in outside diameter. Most preferably, the microspheres are about 50 microns in outside diameter.

The microspheres of the invention may be prepared by various processes, as will be readily apparent to those skilled in the art, once armed with the present disclosure, such as by interfacial polymerization, phase separation and coacervation, multiorifice centrifugal preparation, and solvent evaporation. Suitable procedures which may be employed or modified in accordance with the present disclosure to prepare microspheres within the scope of the invention include those procedures disclosed in Garner et al., U.S. Pat. No. 4,179,546, Garner, U.S. Pat. No. 3,945,956, Cohrs et al., U.S. Pat. No. 4,108,806, Japan Kokai Tokkyo Koho 62 286534, British Patent No. 1,044,680, Kenaga et al., U.S. Pat. No. 3,293,114, Morehouse et al., U.S. Pat. No. 3,401,475, Walters, U.S. Pat. No. 3,479,811, Walters et al., U.S. Pat. No. 3,488,714, Morehouse et al., U.S. Pat. No. 3,615,972, Baker et al., U.S. Pat. No. 4,549,892, Sands et al., U.S. Pat. No. 4,540,629, Sands et al., U.S. Pat. No. 4,421,562, Sands, U.S. Pat. No. 4,420,442, Mathiowitz et al., U.S. Pat. No. 4,898,734, Lencki et al., U.S. Pat. No. 4,822,534, Herbig et al., U.S. Pat. No. 3,732,172, Himmel et al., U.S. Pat. No. 3,594,326, Sommerville et al., U.S. Pat. No. 3,015,128, Deasy, *Microencapsulation and Related Drug Processes*, Vol. 20, Chs. 9 and 10, pp. 195-240 (Marcel Dekker, Inc., N.Y., 1984), Chang et al., *Canadian J. of Physiology and Pharmacology*, Vol. 44, pp. 115-129 (1966), and Chang, *Science*, Vol. 146, pp. 524-525 (1964), the disclosures of each of which are incorporated herein by reference in their entirety.

In accordance with the preferable synthesis protocol, the microspheres are prepared using a heat expansion process such as is described in Garner et al., U.S. Pat. No. 4,179,546, Garner, U.S. Pat. No. 3,945,956, Cohrs et al., U.S. Pat. No. 4,108,806, British Patent No. 1,044,680, and Japan Kokai Tokkyo Koho 62 286534. In general terms, the heat expansion process is carried out by preparing microspheres of an expandable polymer or copolymer which contain in their void (cavity) a volatile liquid. The microsphere is then heated, plasticising the microsphere and volatilizing the gas, causing the microsphere to expand to up to about several times its original size. When the heat is removed, the thermoplastic polymer retains at least some of its expanded shape. Microspheres produced by this process tend to be of particularly low density, and are thus preferred. The foregoing described process is well known in the art, and is referred to herein as the heat expansion process for preparing low density microspheres.

Polymers useful in the heat expansion process will be readily apparent, to those skilled in the art and include thermoplastic polymers or copolymers, including polymers or copolymers of many of the monomers described above. Preferable of the polymers and copolymers described above include the following copolymers: polyvinylidene-polyacrylonitrile, polyvinylidene-polyacrylonitrile-polymethylmethacrylate, and polystyrene-polyacrylonitrile. A most preferred copolymer is polyvinylidene-polyacrylonitrile.

Volatile liquids useful in the heat expansion process will also be well known to those skilled in the art and include: aliphatic hydrocarbons such as ethane, ethylene, propane, propene, butane, isobutane, neopentane, acetylene, hexane, heptane; chlorofluorocarbons such as

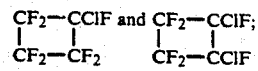

tetraalkyl silanes such as tetramethyl silane, trimethylethyl silane, trimethylisopropyl silane, and trimethyl n-propyl silane; as well as perfluorocarbons such as those having between 1 and about 9 carbon atoms and between about 4 and about 20 fluorine atoms, especially $C_4F_{10}$. In general, it is important that the volatile liquid not be a solvent for the microsphere polymer or copolymer. The volatile liquid should also have a boiling point that is below the softening point of the microsphere polymer or co-polymer. Boiling points of various volatile liquids and softening points of various polymers and copolymers will be readily ascertainable to one skilled in the art, and suitable combinations of polymers or copolymers and volatile liquids will be easily apparent to the skilled artisan. By way of guidance, and as one skilled in the art would recognize, generally as the length of the carbon chain of the volatile liquid increases, the boiling point of that liquid increases. Also, by mildly preheating the microspheres in water in the presence of hydrogen peroxide prior to definitive heating and expansion may pre-soften the microsphere to allow expansion to occur more readily.

For example, to produce microspheres of the present invention, vinylidene and acrylonitrile may be copolymerized in a medium of isobutane liquid using one or more of the foregoing modified or unmodified literature procedures, such that isobutane becomes entrapped within the microspheres. When such microspheres are then heated to between about 80° C. and about 120° C., the isobutane gas expands, which in turn expands the microspheres. After heat is removed, the expanded polyvinylidene and acrylonitrile copolymer microspheres remain substantially fixed in their expanded position. The resulting low density microspheres are extremely stable both dry and suspended in an aqueous media. Isobutane is utilized merely as an illustrative liquid, with the understanding that other liquids which undergo liquid/gas transitions at temperatures useful for the synthesis of these microspheres and formation of the very low density microspheres upon heating can be substituted for isobutane. Similarly, monomers other than vinylidene and acrylonitrile may be employed in preparing the microsphere.

Most preferably, the low density microspheres employed are those commercially available from Expancel, Nobel Industries, Sundsvall, Sweden, such as the EXPANCEL 551 DE ™ microspheres. The EXPANCEL 551 DE ™ microspheres are composed of a copolymer of vinylidene and acrylonitrile which have encapsulated therein isobutane liquid. Such microspheres are sold as a dry composition and are approximately 50 microns in size. The EXPANCEL 551 DE ™ microspheres have a specific gravity of only 0 02 to 0.05, which is between one-fiftieth and one-twentieth the density of water.

In one embodiment, the microspheres of the present invention are gas-filled. By gas-filled, it is meant that at least part of the void volume inside the microspheres is occupied by the gas. Preferably, substantially all of the void volume inside the microspheres is occupied by the gas. The gas may be any type of gas, such as, for example, carbon dioxide, oxygen, nitrogen, xenon, argon, neon, helium and air. Preferably, the gas is carbon dioxide, oxygen, nitrogen, xenon, argon, neon and helium. Most preferably, the gas is inert, that is, a gas that is substantially resistant to chemical or physical action. The gas-filled low density microspheres may be synthesized under pressure such that gases are solubilized in the liquid employed in microsphere synthesis. When the pressure is removed, the gas comes out of solution to fill the microsphere void. Such microspheres can further be subjected to a heat expansion process, as described above.

For example, to produce the gas-filled microspheres of the invention, one may copolymerize vinylidene and acrylonitrile using one or more of the foregoing procedures, such as phase separation/coacervation techniques in a pressurized and/or low temperature environment (e.g., at about 300 psi, and/or at about 0° C.) with a high concentration of dissolved gas (e.g., dissolved nitrogen) in solution, to form a large microsphere containing the dissolved gas. When the pressure is removed and/or the temperature raised, the gas bubbles come out of solution, forming gas filled microspheres. Such microspheres can further be subjected to a heat expansion process, as described above.

It is preferable that the microspheres be relatively stable in the gastrointestinal tract or other body cavities during the length of time necessary for completing an imaging examination. Low density microspheres prepared from the aforementioned monomer and polymer compositions will provide such stable microspheres.

In order for these microspheres to serve as effective CT contrast agents, it is necessary for the microspheres to be mixed in solution in a substantially homogeneous suspension. This can be accomplished by using thickening and suspending agents. A wide variety of thickening and suspending agents may be used to a prepare the substantially homogeneous suspensions of the microspheres. Suitable thickening and suspending agents, for example, include any and all biocompatible agents known in the art to act as thickening and suspending agents. Particularly useful are the natural thickening and suspending agents alginates, xanthan gum, guar, pectin, tragacanth, bassorin, karaya, gum arabic, casein, gelatin, cellulose, sodium carboxymethylcellulose, methylcellulose, methylhydroxycellulose, bentonite, colloidal silicic acid, and carrageenin, and the synthetic thickening and suspending agents polyethylene glycol, polypropylene glycol, and polyvinylpyrrolidone. As those skilled in the art would recognize, once armed with the present disclosure, the suspending agents may be formulated, if desired, to be either less dense than water or of neutral density, so as to not subtract from the density lowering capabilities of the microspheres. For example, a cellulose suspension may have a somewhat lower density than water, e.g., a 2 weight % cellulose solution with 0.25 weight % xanthan gum has a density of 0.95. The thickening and suspending agents may be employed in varying amounts, as those skilled in the art would recognize, but preferably are employed in amounts of about 0.25 to about 10 weight % preferably about 0.5 to about 5 weight % of the contrast medium.

The substantially homogeneous, aqueous suspension of low density microspheres of the invention are useful as CT contrast agents. These agents are capable of producing negative contrast in the gastrointestinal tract or in other body cavities, providing effective contrast enhancement and improved visualization in these areas of the body. Specifically, the present invention is directed to a method of providing an image of or detecting diseased tissue in the gastrointestinal region and other body cavities of a patient, the method comprising administering to the patient a contrast medium comprising a substantially homogeneous aqueous solution of low density microspheres, and scanning the patient using computed tomography imaging to obtain visible images of the gastrointestinal region or other body cavities or of diseased tissue in these areas of the body.

The phrase gastrointestinal region or gastrointestinal tract, as used herein, includes the region of a patient defined by the esophagus, stomach, small and large intestines, and rectum. The phrase other body cavities, as used herein, includes any region of the patient, other than the gastrointestinal region, having an open passage, either directly or indirectly, to the external environment, such regions including the sinus tracts, the fallopian tubes, the bladder, etc. The patient can be any type of mammal, but most preferably is a human.

As one skilled in the art would recognize, administration of the contrast medium to the patient may be carried out in various fashions, such as orally, rectally, or by injection. When the region to be scanned is the gastrointestinal region, administration of the contrast medium of the invention is preferably carried out orally or rectally. When other body cavities such as the fallopian tubes or sinus tracts are to be scanned, administration is preferably by injection. As would also be recognized by one skilled in the art, wide variations in the amounts of the gas filled microspheres can be employed in the methods and kits of the invention, with the precise amounts varying depending upon such factors as the mode of administration (e.g., oral, rectal, by injection), and the specific body cavity and portion thereof for which an image is sought (e.g., the stomach of the gastrointestinal tract). Typically, dosage is initiated at lower levels and increased until the desired contrast enhancement is achieved.

For CT imaging, it is generally desirable to decrease the density of the lumen of the gastrointestinal tract or other body cavities to at least about $-30$ HU, the maximum decrease being limited by the practical amount of the microspheres which may be suspended in the aqueous media and ingested by the patient. In general, a decrease in HU to between about $-30$ HU and about $-150$ HU is sufficient to mark the inside of the bowel or other body cavity. By way of general guidance, and as a rough rule of thumb, to decrease the density of the microsphere aqueous suspension to about −150 HU, the microspheres must occupy about 15% of the total volume of the aqueous suspension. To achieve a density of about −50 HU, the microspheres must occupy about 5% of the total volume of the solution. The volume of contrast agent administered to the patient is typically between about 50 to about 1000 cc. Using the EXPANCEL 551 DE ™ microspheres as a model, it has been found that about 0.6 grams of the dry 50 micron spheres in 100 cc of aqueous suspension is sufficient to decrease the density of the suspension to nearly −150 HU.

It should be noted that smaller microspheres are generally more stable in suspension, but usually have higher specific gravity than larger microspheres. Therefore, for CT, the size and particular microspheres, as well as the suspending media (thickening and suspending agents) should selected to minimize specific gravity, while maximizing the stability of the suspension.

The contrast medium utilized of the present invention may also be employed with other conventional additives suitable for use in the applications contemplated for the subject invention.

Where gastrointestinal applications are concerned, such additives include conventional biocompatible anti-gas agents, osmolality raising agents, gastrointestinal transit agents (the later agents serving to decrease the gastrointestinal transit time and increase the rate of gastrointestinal emptying) and, in some instances, gas-forming agents.

As used herein the term anti-gas agent is a compound that serves to minimize or decrease gas formation, dispersion and/or adsorption. A number of such agents are available, including antacids, antiflatulents, antifoaming agents, and surfactants. Such antacids and antiflatulents include, for example, activated charcoal, aluminum carbonate, aluminum hydroxide, aluminum phosphate, calcium carbonate, dihydroxyaluminum sodium carbonate, magaldrate magnesium oxide, magnesium trisilicate, simethicone, sodium carbonate, loperamide hydrochloride, diphenoxylate, hydrochloride with atropine sulfate, Kaopectate ™ (kaolin) and bismuth salts. Suitable antifoaming agents useful as anti-gas agents include simethicone, protected simethicone, siloxyalkylene polymers, siloxane glycol polymers, polyoxypropylene-polyoxyethylene copolymers, polyoxyalkylene amines and imines, branched polyamines, mixed oxyalkylated alcohols, finely divided silica either alone or mixed with dimethyl polysiloxane, sucroglycamides (celynols), polyoxylalkylated natural oils, halogenated silicon-containing cyclic acetals, lauryl sulfates, 2-lactylic acid esters of unicarboxylic acids, triglyceride oils. Particles of polyvinyl chloride or silica may also function as anti-foaming agents in the subject invention. Suitable surfactants include perfluorocarbon surfactants, such as, for example, DuPont Zonyl ™ perfluoroalkyl surfactants known as Zonyl ™ RP or Zonyl ™ NF, available from DuPont, Chemicals and Pigments Division, Jackson Laboratory, Deepwater, N.J. 08023. Of course, as those skilled in the art will recognize, any anti-gas agents employed must be suitable for use within the particular biological system of the patient in which it is to be used. The concentration of such anti-gas agents may vary widely, as desired, as will be readily apparent to those skilled in the art. Typically, however, such agents are employed in concentrations of between about 20 and about 2000 ppm, most preferably in concentrations between about 50 and about 1000 ppm.

Suitable osmolality raising agents include polyols and sugars, for example, mannitol, sorbitol, arabitol, xylitol, glucose, sucrose, fructose, dextrose, and saccharine, with mannitol and sorbitol being most preferred. The concentration of such osmolality raising agents may vary, as desired, however, generally a range of about 5 to about 70 g/l, preferably about 30 to about 50 g/l of the contrast medium. Such compounds may also serve as sweeteners for the ultimate formulation, if desired.

Gastrointestinal transit agents include algin, as well as many of the compounds listed above as thickening and suspending agents, with algin being most preferred. The amount of such agents will, of course, vary as those skilled in the art will recognize, but generally will be employed in an amount of between about 5 and about 40 mmol/l.

In some applications, it may be helpful to incorporate gas-forming agents into the contrast medium. Gas-forming agents include sodium bicarbonate, calcium carbonate, aminomalonate, and the like, which will form gas, for example, upon introduction into the gastrointestinal tract. Such gas-forming agents will serve to distend the gastrointestinal tract and create a form of "double contrast" between the gas and the low density microspheres.

Kits useful for computed tomography imaging of the gastrointestinal region or other body cavities in accordance with the present invention comprise low density microspheres, and a thickening or suspending agent, in addition to conventional computed tomography imaging kit components. Such conventional computed tomography kit components will be readily apparent to those skilled in the art, once armed with the present disclosure.

Where imaging of the gastrointestinal region is contemplated, such computed tomography kit components may include, for example, anti-gas agents, osmolality raising agents, gastrointestinal transit agents and, in some instances, gas-forming agents.

The computed tomography imaging principles and techniques which are employed are conventional and are described, for example, in *Computed Body Tomography*, Lee, J. K. T., Sagel, S. S., and Stanley, R. J., eds., Ch. 1, pp. 1-7 (Raven Press, N.Y. 1933). Any of the various types of computed tomography imaging devices can be used in the practice of the invention, the particular type or model of the device not being critical to the method of the invention.

The present invention is further described in the following Examples. Examples 1-7 are prophetic examples based at least in part on the teachings of Garner, U.S. Pat. No. 3,945,956, and describe the preparation of microspheres by a heat expansion process. Examples 8-9 are actual examples that describe the preparation of contrast media of the invention. The following Examples are not to be construed as limiting the scope of the appended claims.

EXAMPLES

Example 1

A vessel is filled with 50 parts by weight of deionized water and 6 parts by weight of a 25 percent by weight aqueous colloidal silica dispersion. A mixture of 0.3 parts by weight of a 10 weight percent solution of diethylamine-adipic acid copolymer is added to the above. A condensation reaction occurs creating a mixture having a viscosity of about 95 centipoise at a temperature of about 27° C. Potassium dichromate (0.05 parts by weight) is added to the aqueous phase as a water phase polymerization inhibitor. Sodium chloride (1 part by weight) is also present in the water phase; hydrochloric acid is used to adjust the pH of the aqueous phase to 4.0. Styrene (15 parts by weight), acrylonitrile (10 parts by weight), a mixture of diethylbenzene and divinylbenzene (0.21 parts by weight comprising a 55:45 percent mixture of each respectively), 6.25 parts by weight of isobutane and 0.07 parts by weight of secondary butyl peroxydicarbonate. The oil phase is added to the water phase with violent agitation created by a shearing blade rotating at 10,000 RPM employing a mixing blender. After the material has reacted for about 30 minutes, the mixture is poured into a citrate bottle and capped. The material is maintained at about 50° C. in the citrate bath for about 24 hours and agitated throughout this time. At the end of 24 hours, the reaction bottle is cooled and the material is removed, washed and dried. A portion of the microspheres are set aside and the remainder are heated in an air oven for a period of about 30 minutes at about 150° C. A sample of the dry unexpanded and dry expanded microspheres are then studied by a Coulter Counter. The dry unexpanded microspheres have a size of about 2 to 12 microns. About half of the microspheres exposed to the heating process show expansion.

Example 2

The procedures of Example 1 are substantially repeated with the exception that 1 part by weight of methanol is added to the reaction mixture. The dry unexpanded and dry heat expanded microspheres are then studied by Coulter Counter. The dry unexpanded microspheres measure about 8 to 10 microns in size. Essentially all the microspheres exposed to heat expand.

Example 3

The procedures of Example 2 are substantially repeated except that after synthesis of the microspheres, a slurry of the microspheres is added to an aqueous solution containing 35 weight percent hydrogen peroxide. This slurry is heated to a temperature of about 50° C. for about 3.5 hours and subsequently cooled and air-dried. A portion of the microspheres is then added to water and heated to a temperature of about 75° C. with vigorous stirring for about 30 seconds. Study with Coulter Counter shows that pretreatment with hydrogen peroxide enables a lower temperature and briefer period of heating to be used for definitive heating and expansion.

Example 4

The procedures of Example 1 are substantially repeated with the exception that 5 parts by weight of ethanol are included in the reaction mixture forming the microspheres. Coulter Counter shows that the dry unexpanded particles have diameters of about 24 to 28 microns. When heated, essentially all of the microspheres expand.

Example 5

The procedures of Example 1 are substantially repeated with the exception that in place of methanol, 1 part by weight of normal butanol is used. The diameter of the dry unexpanded microspheres is about 10 to 12 microns and on heating, essentially all of the microspheres expand.

Example 6

The procedures of Example 1 are substantially repeated with the exception that the volatile liquid isobutane is replaced with perfluorocarbon liquid ($C_4F_{10}$). The remainder of the process is similar. The resulting microspheres are filled with perfluorocarbon liquid rather than isobutane.

Example 7

The procedures of Example 1 are substantially repeated with the exception that the reaction is conducted in a pressurized vessel enabling pressurization with gas and simultaneous agitation (agitation accomplished with either sonication or shearing blades within the device). As the microspheres are formed within the device, the vessel is pressurized to about 300 psi with nitrogen gas. The vessel is then depressurized, allowing the gas to come out of solution. The microspheres are then subjected to heat as substantially described in Example 1.

Example 8

A suspension of 2% of 22 micron fiber length cellulose in 0.25% xanthan gum in water was prepared Scans by CT showed a CT density of about −45 HU for the cellulose suspension. EXPANCEL 551 DE ™ polyvinylidene-polyacrylonitrile microspheres, 50 microns in size, were then suspended in the aqueous cellulose suspension at a concentration of 0.4 grams of microspheres per 100 ml of cellulose suspension using vigorous shaking. The resulting suspension remained substantially homogeneous for about 10 minutes. The suspension was again shaken vigorously to render it substantially homogeneous and scanned immediately by CT. The resulting CT density as measured by the scanner was about −96 HU.

Example 9

A suspension of 1% algin was prepared. EXPANCEL 551 DE ™ microspheres were added to the algin suspension in an amount of about 0.2 grams of microspheres per deciliter of algin suspension, using vigorous shaking, to form a substantially homogeneous suspension. The resulting suspension was found to have much greater stability than the cellulose/microsphere suspension of Example 1. The algin/microsphere suspension was then scanned by CT, with the density as measured by the scanner being about −40 HU.

Various modifications of the invention in addition to those shown and described herein will be apparent to those skilled in the art from the foregoing description. Such modifications are also intended to fall within the scope of the appended claims.

What is claimed is:

1. A method of providing an image of the gastrointestinal region and other body cavities of a patient comprising
    (a) administering to the patient a contrast medium comprising a substantially homogeneous aqueous suspension of low density microspheres having an internal void volume of at least about 75% of the total volume of the microsphere, and
    (b) scanning the patient using computed tomography imaging to obtain visible images of the gastrointestinal region or other body cavities.

2. A method according to claim 1 wherein said microspheres comprise synthetic polymers or copolymers prepared from the group of monomers consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethyl methacrylate, vinyl pyridine, aminoethyl methacrylates, 2-methacryloyloxytrimethylammonium chloride, N,N'-methylenebisacrylamide, ethylene glycol dimethacrylates, 2,2'-(p-phenylenedioxy)-diethyl dimethacrylate, divinylbenzene, triallylamine, and methylenebis-(4-phenyl-isocyanate).

3. A method according to claim 2 wherein said microspheres comprise synthetic polymers or copolymers prepared from the group of monomers consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethylmethacrylate, vinyl pyridine, aminoethyl methacrylates, and 2-methacryloyloxytrimethylammonium chloride.

4. A method according to claim 1 wherein said microspheres comprise synthetic polymers or copolymers selected from the group consisting of polyacrylic acid, polyethyleneimine, polymethacrylic acid, polymethylmethacrylate, polysiloxane, polydimethylsiloxane, polylactic acid, poly(ε-capro-lactone), epoxy resin, poly(ethylene oxide), poly(ethylene glycol), polyamide, polyvinylidene-polyacrylonitrile, polyvinylidene-polyacrylonitrile-polymethylmethacrylate, and polystyrene-polyacrylonitrile.

5. A method according to claim 4 wherein said microspheres comprise polyvinylidene-polyacrylonitrile copolymer.

6. A method according to claim 1 wherein said microspheres are prepared by a heat expansion process.

7. A method according to claim 1 wherein said microspheres are gas-filled.

8. A method according to claim 7 wherein said gas in said gas-filled microspheres is selected from the group consisting of carbon dioxide, oxygen, nitrogen, xenon, argon, neon, and helium.

9. A method for diagnosing the presence of diseased tissue in the gastrointestinal region or other body cavities of a patient comprising
(a) administering to the patient a contrast medium comprising a substantially homogeneous aqueous suspension of low density microspheres having an internal void volume of at least about 75% of the total volume of the microsphere, and
(b) scanning the patient using computed tomography imaging to obtain visible images of any diseased tissue in the patient.

10. A method according to claim 9 wherein said microspheres comprise synthetic polymers or copolymers prepared from the group of monomers consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethylmethacrylate, vinyl pyridine, aminoethyl methacrylates, 2-methacryloyloxytrimethylammonium chloride, N,N'-methylenebisacrylamide, ethylene glycol dimethacrylates, 2,2'-(p-phenylenedioxy)-diethyl dimethacrylate, divinylbenzene, triallylamine, and methylenebis-(4-phenyl-isocyanate).

11. A method according to claim 10 wherein said microspheres comprise synthetic polymers or copolymers prepared from the group of monomers consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethylmethacrylate, vinyl pyridine, aminoethyl methacrylates, and 2-methacryloyloxytrimethylammonium chloride.

12. A method according to claim 9 wherein said microspheres comprise synthetic polymers or copolymers selected from the group consisting of polyacrylic acid, polyethyleneimine, polymethacrylic acid, polymethylmethacrylate, polysiloxane, polydimethylsiloxane, polylactic acid, poly(ε-capro-lactone), epoxy resin, poly(ethylene oxide), poly(ethylene glycol), polyamide, polyvinylidene-polyacrylonitrile, polyvinylidene-polyacrylonitrile-polymethylmethacrylate and polystyrene-polyacrylonitrile.

13. A method according to claim 12 wherein said microspheres comprise polyvinylidene-polyacrylonitrile copolymer.

14. A method according to claim 9 wherein said microspheres are prepared by a heat expansion process.

15. A method according to claim 9 wherein said microspheres are gas-filled.

16. A method according to claim 15 wherein said gas in said gas-filled microspheres is selected from the group consisting of carbon dioxide, oxygen, nitrogen, xenon, argon, neon, and helium.

* * * * *

UNITED STATES PATENT AND TRADEMARK OFFICE
CERTIFICATE OF CORRECTION

PATENT NO. : 5,281,408
DATED : January 25, 1994
INVENTOR(S) : Evan C. Unger

It is certified that error appears in the above-identified patent and that said Letters Patent is hereby corrected as shown below:

Column 3, line 20, delete "micrcns" and insert --microns--.

Column 10, line 25, after "prepared" insert a period.

Signed and Sealed this

Twenty-eight Day of March, 1995

Attest:

BRUCE LEHMAN

Attesting Officer    Commissioner of Patents and Trademarks